US010039674B2

(12) United States Patent
Wada

(10) Patent No.: US 10,039,674 B2
(45) Date of Patent: Aug. 7, 2018

(54) CONVEYANCE DEVICE

(71) Applicant: ZUIKO CORPORATION, Settu-shi, Osaka (JP)

(72) Inventor: Takao Wada, Settu (JP)

(73) Assignee: ZUIKO CORPORATION, Settu-Shi, Osaka (JP)

(*) Notice: Subject to any disclaimer, the term of this patent is extended or adjusted under 35 U.S.C. 154(b) by 109 days.

(21) Appl. No.: 15/033,381

(22) PCT Filed: Oct. 30, 2014

(86) PCT No.: PCT/JP2014/078990
§ 371 (c)(1),
(2) Date: Apr. 29, 2016

(87) PCT Pub. No.: WO2015/068641
PCT Pub. Date: May 14, 2015

(65) Prior Publication Data
US 2016/0256331 A1 Sep. 8, 2016

(30) Foreign Application Priority Data
Nov. 8, 2013 (JP) ................. 2013-231744

(51) Int. Cl.
B65G 47/244 (2006.01)
A61F 13/15 (2006.01)
(Continued)

(52) U.S. Cl.
CPC .. *A61F 13/15764* (2013.01); *A61F 13/15723* (2013.01); *B26D 1/40* (2013.01);
(Continued)

(58) Field of Classification Search
CPC ............... B65G 47/244; B65G 47/848; B65H 2301/33216; A61F 13/15764
See application file for complete search history.

(56) References Cited

U.S. PATENT DOCUMENTS 4,275,807 A * 6/1981 Mohn .................. B65C 9/04
198/377.01
4,799,414 A 1/1989 Scheffer et al.
(Continued)

FOREIGN PATENT DOCUMENTS

EP 2659868 A1 11/2013
JP S64-38377 A 2/1989
JP 2006-230438 A 9/2006

OTHER PUBLICATIONS

"Gears and gear ratios" Nov. 19, 2012, author unknown.*
(Continued)

*Primary Examiner* — Kenneth E Peterson
(74) *Attorney, Agent, or Firm* — Manabu Kanesaka

(57) ABSTRACT

In a conveyance device, first and second travel members that hold pads are arranged alternately and travel along the outer peripheral surface of a stationary drum in conjunction with the rotation of a drive member. One or both of the first and second travel members have a rotatably supported shaft member having an engaging section that engages with a guide section formed in the outer peripheral surface of the stationary drum. The rotation of the shaft member is transmitted to the pads and the pads rotate. When conveyance articles are released from pads that have received conveyance articles having the same orientation, the orientation of conveyance articles released from first pads held by the first travel member is different from the orientation of the conveyance articles released from the second pads held by the second travel member.

4 Claims, 13 Drawing Sheets

(51) Int. Cl.
    *B26D 1/40*         (2006.01)
    *B65G 47/84*       (2006.01)
    *B65H 29/24*       (2006.01)

(52) U.S. Cl.
    CPC .......... *B26D 1/405* (2013.01); *B65G 47/244* (2013.01); *B65G 47/848* (2013.01); *B65H 29/241* (2013.01); *B65H 2301/33216* (2013.01); *B65H 2301/33222* (2013.01); *B65H 2301/4472* (2013.01); *B65H 2801/57* (2013.01); *Y10T 83/648* (2015.04)

(56) References Cited

U.S. PATENT DOCUMENTS

| | | | |
|---|---|---|---|
| 4,962,683 | A | 10/1990 | Scheffer et al. |
| 5,025,910 | A | 6/1991 | Lasure et al. |
| 5,447,219 | A | 9/1995 | Dworak et al. |
| 5,871,079 | A | 2/1999 | Nannini et al. |
| 5,988,354 | A * | 11/1999 | Spatafora ............... B65G 29/00 198/374 |
| 6,736,923 | B1 | 5/2004 | Franzmann et al. |
| 9,150,321 | B2 * | 10/2015 | Schneider ......... A61F 13/15764 |
| 2008/0196564 | A1 | 8/2008 | McCabe |
| 2013/0270069 | A1 | 10/2013 | Papsdorf |

OTHER PUBLICATIONS

Europe Patent Office, "Search Report for European Patent Application No. 14860620.5," dated Jun. 19, 2017.
PCT International Search Report of PCT/JP2014/078990.

* cited by examiner (a)

(b)

--Prior Art--

--Prior Art--

FIG. 12   --Prior Art--
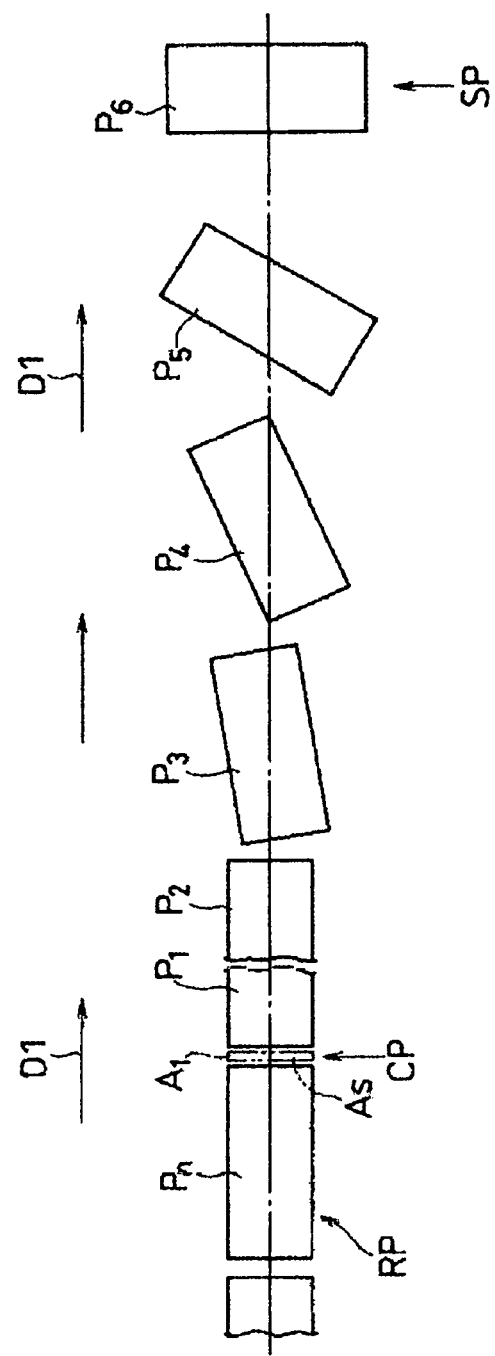

FIG. 13 --Prior Art--
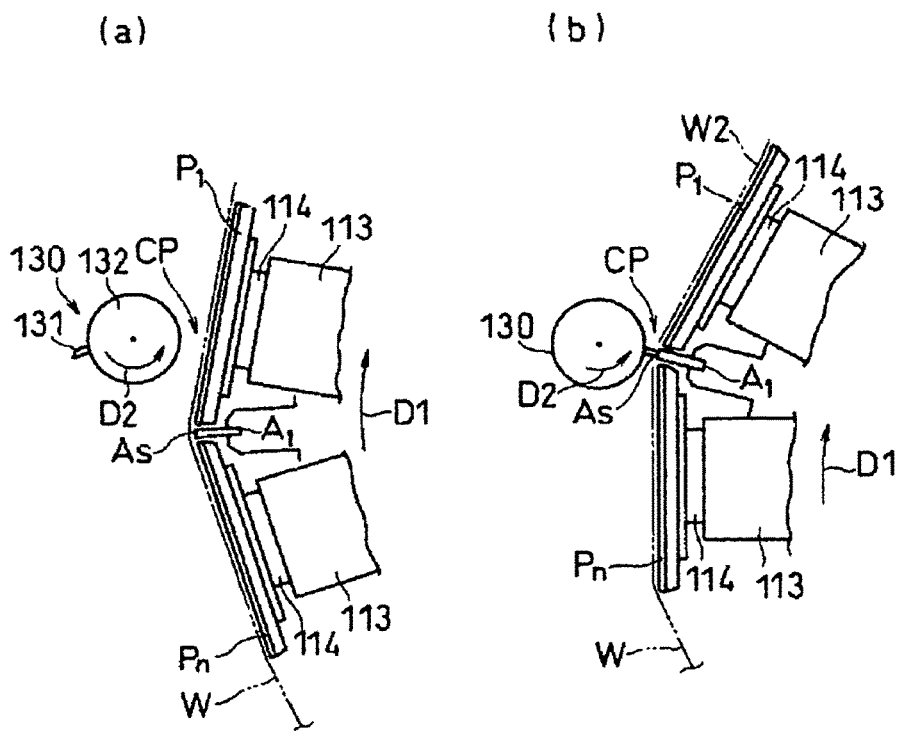
FIG. 14 --Prior Art--
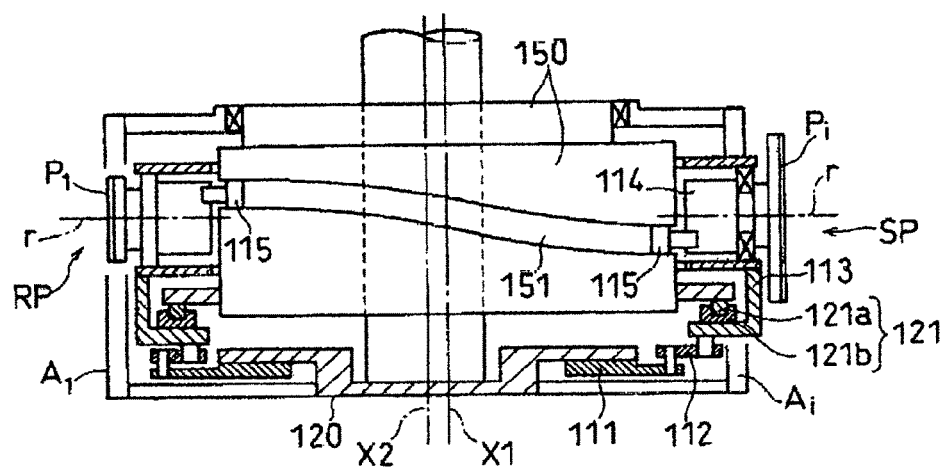

CONVEYANCE DEVICE

RELATED APPLICATIONS

The present application is National Phase of International Application No. PCT/JP2014/078990 filed Oct. 30, 2014, and claims priority from Japanese Application No. 2013-231744, filed Nov. 8, 2013.

TECHNICAL FIELD

The present invention relates to a conveyance device and, in particular, to a conveyance device in which transfer is performed with changing the orientations of conveyed articles.

BACKGROUND OF THE INVENTION

In the conventional art, in production of disposable underpants, disposable diapers, or the like, a conveyance device serving also as a web cutting device is employed that, after cutting a web, conveys individual cut pieces and changes the orientations of the individual pieces during the conveyance.

An example of such a device is shown, for example, in FIGS. 10 to 14. FIG. 11 is a schematic perspective view showing the state of carrying a web. As shown in FIG. 11, a web W is conveyed along the cylindrical outer peripheral surface of a stationary drum indicated by a dashed dotted line, in the circumferential direction indicated by an arrow D1 and then the web W is cut. Then, individual pieces W2 obtained by cutting are conveyed with changing the orientation, and then transferred to a subsequent device at a delivery position SP.

FIG. 10 is a schematic diagram showing the configuration of a conveyance device. FIG. 14 is a sectional diagram showing the configuration of a conveyance device. As shown in FIGS. 10 and 14, a plurality of travel members 113 are held in a freely movable manner along the outer peripheral surface of a stationary drum 150. Anvils A1, A2, . . . , Ai, . . . , An moving together with the travel members 113 are arranged between the travel members 113 adjacent to each other.

Each travel member 113 supports in a revolvable manner a shaft member 114 whose center axis r extends in a radial direction of the stationary drum 150. In the shaft member 114, a pad P1, P2, . . . , Pi, . . . , Pn for vacuum-holding the web W is fixed to one end on the radial-directional outer side of the stationary drum 150. Further, a cam follower 115 for engaging with a cam groove 151 formed in the outer peripheral surface of the stationary drum 150 is formed at the other end on the radial-directional center side of the stationary drum 150. In the travel member 113, a groove member 121b for engaging with a protruding part 121a fixed to the stationary drum 150 is fixed and then the protruding part 121a and the groove member 121b constitute a guiding part 121 for guiding the travel member 113. Then, the travel member 113 is held in a freely movable manner along the outer peripheral surface of the stationary drum 150.

The travel member 113 is linked through links 111 and 112 to a revolving body 120 and moves along the outer peripheral surface of the stationary drum 150 in association with revolution of the revolving body 120. At that time, the cam follower 115 formed at the other end of the shaft member 114 supported in a rotatable manner by the travel member 113 engages with the cam groove 151 formed in the outer peripheral surface of the stationary drum 150. Thus, the shaft member 114 reciprocally rotates about the center axis r within a range of 90°. By virtue of this, as shown in a developed view of FIG. 12, the orientations of pads P1, P2, . . . , Pn vary within a range of 90° between a parallel direction and a perpendicular direction relative to the moving direction indicated by a dashed dotted line, that is, the circumferential direction of the outer peripheral surface of the stationary drum.

FIGS. 13(a) and 13(b) are main part enlarged views at the time of web cutting. As shown in FIGS. 12, 13(a), and 13(b), the web W is conveyed from a receiving position RP to a cutting position CP in the direction of arrow D1. A cutting unit 130 is arranged such as to face the cutting position CP. In the cutting unit 130, a cutter 131 is fixed to a revolving member 132. The revolving member 132 revolves in the direction of arrow D2 in synchronization with conveyance of the web W. As shown in FIG. 13(b), in the web W, when a portion extending between the two pads Pn and P1 passes the cutting position CP, the portion is pinched between the tip surface As of the anvil A1 and the blade edge of the cutter 131 so as to be cut.

As shown in FIG. 14, the center axis X1 of the stationary drum 150 and the center axis X2 of the revolving body 120 are distant from each other. The anvils A1, A2, . . . , An are held in a freely movable manner along a cylindrical surface coaxial to the center axis X2 of the revolving body 120 and then, as shown in FIG. 10, at the delivery position SP, retract from the conveyance path for the web moved and held by the pad Pi (for example, see Patent Document 1).

PRIOR ART REFERENCES

Patent Documents

Patent Document 1: Japan Patent Publication No. 4745061

SUMMARY OF THE INVENTION

Problem to be Solved by the Invention

For example, in a case that the thickness of each individual piece obtained by cutting from the web is not uniform and hence a thin portion and a thick portion occur, the individual pieces may be stacked on each other with alternately changing the orientations of the individual pieces such that the thin portions themselves or the thick portions themselves may be not overlaid on each other. By virtue of this, the individual pieces can be stacked orderly. In such a case, a conveyance device would be employed that transfer is performed with alternately changing the orientations of the individual pieces obtained by cutting.

Nevertheless, for example, when a configuration is employed that two cam grooves are formed in a stationary drum and then pads whose orientations are changed to one direction by one cam groove and pads whose orientations are changed to the other direction by the other cam groove are provided, the configuration of the conveyance device becomes complicated.

In view of such situations, a problem to be solved by the present invention is to provide a conveyance device and a conveyance method in which transfer can be performed with alternately changing the orientations of the conveyed articles by employing a simple configuration.

Means for Solving the Problem

The present invention for resolving the above-mentioned problem provides a conveyance device having the following construction.

A conveyance device includes: (a) a guiding part formed in a cylindrical outer peripheral surface; (b) a plurality of first travel members arranged along the outer peripheral surface and moving in a circumferential direction of the outer peripheral surface; (c) second travel members in the same number as the number of the first travel members, that are arranged between the first travel members adjacent to each other and that move in the circumferential direction together with the first travel members; (d) a plurality of pads that are individually held by the first and the second travel members and move together with the first and the second travel members and that start holding of a conveyed article at a receiving position and then release the holding of the conveyed article at a delivery position; and (e) a plurality of pad rotating mechanisms provided in individual travel members of either or both of the first and the second travel members. The pad rotating mechanism includes a shaft member. The shaft member is supported by each of the travel members in a revolvable manner, then moves together with each of the travel members, then includes an engagement part engaging with the guiding part, and then revolves in association with movement of each of the travel members. The pad rotating mechanisms individually rotate the pad held by each of the travel members about a shaft center extending in a radial direction of the outer peripheral surface in association with revolution of the shaft member so that in accordance with a difference in the rotation of the pad held by the first travel member and the pad held by the second travel member, orientations of the conveyed articles which were the same in the pads at the receiving position are made different in the pad held by the first travel member and in the pad held by the second travel member at the delivery position.

According to the above-mentioned configuration, the conveyed articles are conveyed from the receiving position to the delivery position in a state of being held by the pads. The number of pads held by the first travel members and the number of pads held by the second travel members are the same as each other and hence the total number of pads is even. At the time of transfer of the conveyed articles, the conveyed article held by the pad of the first travel member and the conveyed article held by the pad of the second travel member are oriented in different directions from each other. Thus, transfer can be performed with alternately changing the orientations of the conveyed articles. The guiding part is common to each other and the pad rotating mechanism for alternately changing the orientations of the conveyed articles is provided merely at least in one group of the travel members. Thus, the orientations of the conveyed articles at the time of transfer of the conveyed articles can be changed by employing a simple configuration.

In a preferable mode, the conveyed article is a continuous web. The conveyance device further includes: (e) a plurality of anvils arranged between the first and the second travel members adjacent to each other and moving together with the first and the second travel members in the circumferential direction; (f) a revolving member that is arranged, with an interval in between, opposite to the web moved in a state of being held by the pads and that revolves in synchronization with movement of the anvils; and (g) a cutter which is held by the revolving member and includes a blade edge protruding to an outer side of the revolving member and in which the blade edge becomes such as to face the anvil in association with revolution of the revolving member. A portion of the web held by the pads and extending between the pads adjacent to each other is pinched between the blade edge of the cutter and the anvil so as to be cut.

In this case, after the web is cut, the individual pieces can be transferred from the pads to the subsequent process in a state that the orientations of the individual pieces serving as conveyed articles obtained by cutting from the web are alternately changed.

Preferably, the pad rotating mechanism transmits the revolution of the shaft member to the pad through a gear wheel.

In this case, such a gear wheel is excellent in durability in comparison with a belt, a chain, or the like and hence is preferable in long-term continuous running.

Preferably, the pad rotating mechanism includes: (i) an identical-directional pad rotating mechanism provided in the first travel member and transmitting the revolution of the shaft member to the pad held by the first travel member, with maintaining an identical direction; and (ii) an opposite-directional pad rotating mechanism provided in the second travel member and transmitting the revolution of the shaft member to the pad held by the second travel member, with converting the revolution into an opposite direction. The pad held by the first travel member and the pad held by the second travel member rotate in opposite directions to each other.

In this case, the angle difference between the pad held by the first travel member and the pad held by the second travel member can be made twice of a case that either alone of the pad held by the first travel member and the pad held by the second travel member rotates with following the guiding part. The guiding part is common to each other and the opposite-directional pad rotating mechanism for converting the revolution of the shaft member into the opposite direction is provided merely in half the number of the travel members. Thus, the orientations of the conveyed articles at the time of transfer of the conveyed articles can alternately be changed by employing a simple configuration.

More preferably, the pad held by the first travel member is fixed coaxially to the shaft member of the identical-directional pad rotating mechanism. The pad held by the second travel member is supported by the second travel member and in a coaxial and relatively rotatable manner relative to the shaft member of the opposite-directional pad rotating mechanism.

In this case, in the first travel member, the configuration of the identical-directional pad rotating mechanism that includes the shaft member and transmits the revolution of the shaft member to the first pad can be simplified. Since the revolving shaft of each of the first and the second pad and the revolving shaft of the shaft member are coaxial to each other, the configuration of realizing opposite rotational directions in the first pad and in the second pad becomes simple.

Preferably, the opposite-directional pad rotating mechanism includes: (i) a first gear wheel revolving integrally with the shaft member held by the second travel member; (ii) a fifth gear wheel revolving integrally with the second pad held by the second travel member; (iii) a second gear wheel supported by the second travel member in a revolvable manner and engaging with the first gear wheel; (iv) a fourth gear wheel supported by the second travel member in a revolvable manner and engaging with the fifth gear wheel; and (v) a third gear wheel engaging with any one of the second gear wheel and the fourth gear wheel and revolving coaxially to and integrally with the other one.

In this case, such a gear wheel is excellent in durability in comparison with a belt, a chain, or the like and hence is preferable in long-term continuous running.

Further, the present invention provides a conveyance method having the following construction.

A conveyance method includes: (i) a first step of, along a cylindrical outer peripheral surface in which a guiding part is formed, moving first and second pads in a same number as each other arranged alternately in a circumferential direction of the outer peripheral surface, in the circumferential direction; (ii) a second step of causing the first and the second pads moving at the first step to start holding of a conveyed article at a receiving position and then release the holding of the conveyed article at a delivery position and thereby conveying the conveyed article from the receiving position to the delivery position; and (iii) a third step of, as for each pad of either or both of the first and the second pads moving at the second step with holding the conveyed article, transmitting, to each of the pads, rotation generated by engagement between an engagement part that moves together with each of the pads and the guiding part, thereby causing each of the pads to rotate and follow the guiding part, so that in accordance with a difference in the rotation of the first and the second pads, orientations of the conveyed articles which were the same in the first and the second pads at the receiving position are made different in the first pad and in the second pad at the delivery position.

In the method described above, the first and the second pads are in the same number as each other. Thus, the total number of pads is even. When either or both of the first and the second pads are rotated with following the guiding part, transfer can be performed with alternately changing the orientations of the conveyed articles by employing a simple configuration.

Preferably, at the third step, the first and the second pads are caused to follow the guiding part and rotate in opposite directions to each other.

In this case, the angle difference between the first and the second pad can be made twice of a case that either alone of the first and the second pads rotates with following the guiding part. The first and the second pads can be rotated by the common guiding part. It is sufficient that a mechanism for converting the rotation into the opposite direction is provided in either of the first and the second pads, that is, in half the number of the pads. Thus, the orientations of the conveyed articles at the time of transfer of the conveyed articles can alternately be changed by employing a simple configuration.

In the method described above, holding of conveyed articles in the form of individual pieces may be started at a receiving position. Alternatively, holding of a continuous conveyed article may be started at a receiving position and then the continuous conveyed article may be made into the form of individual pieces during the conveyance.

In the latter case, preferably, at the first step, a plurality of anvils individually arranged between the first and the second pads adjacent to each other are moved together with the first and the second pads in the circumferential direction of the outer peripheral surface. At the second step, the conveyed article the holding of which performed by the first and the second pads is started is a continuous web. At the third step, the rotation of each of the pads that follows the guiding part is started after each of the pads has passed through a cutting position located between the receiving position and the delivery position. The conveyance method further includes (iv) a fourth step of, in a state that a cutter is held by a revolving member and then the cutter is biased to a predetermined position by a biasing force from a biasing member arranged in the revolving member so that a blade edge of the cutter is caused to protrude, revolving the revolving member in synchronization with movement of the anvils at the first step and then at the cutting position, pinching between the blade edge of the cutter and the anvil a portion of the web conveyed at the second step that extends between the first and the second pads adjacent to each other, so as to cut the portion. At the fourth step, when a reaction force greater than the biasing force acts on the blade edge of the cutter, the biasing member allows the cutter to retract from the predetermined position.

In this case, after the continuous web is cut into the form of individual pieces, the individual pieces can be transferred with alternately changing the orientations. Even when the interval between the cutter and the anvil or the abutting of the blade edge of the cutter varies owing to vibration, thermal deformation, or the like during the operation, at the time of cutting the web, the abutting can be maintained within an appropriate adjustment range. Thus, long-term continuous running becomes easy.

Preferably, at the first step, first and second travel members respectively holding the first and the second pads and alternately arranged along the outer peripheral surface in the circumferential direction are moved in the circumferential direction.

In this case, a configuration of revolving the first and the second pad may be provided in the first and the second travel member so that the configuration can be simplified.

Effect of the Invention

According to the present invention, transfer can be performed with alternately changing the orientations of the conveyed articles by employing a simple configuration.

BRIEF DESCRIPTION OF THE DRAWINGS

FIG. 12 is a developed view showing the states of movement of pads. (Conventional Example 1)

FIGS. 13(a) and 13(b) are main part enlarged views at the time of web cutting. (Conventional Example 1)

FIG. 14 is a sectional diagram showing the configuration of a conveyance device. (Conventional Example 1)

MODE FOR CARRYING OUT THE INVENTION

Embodiments serving as modes of implementation of the present invention are described below with reference to FIGS. 1 to 9.

Embodiment 1

A conveyance device 10 and a conveyance method of Embodiment 1 are described below with reference to FIGS. 1 to 6.

Figure 1:
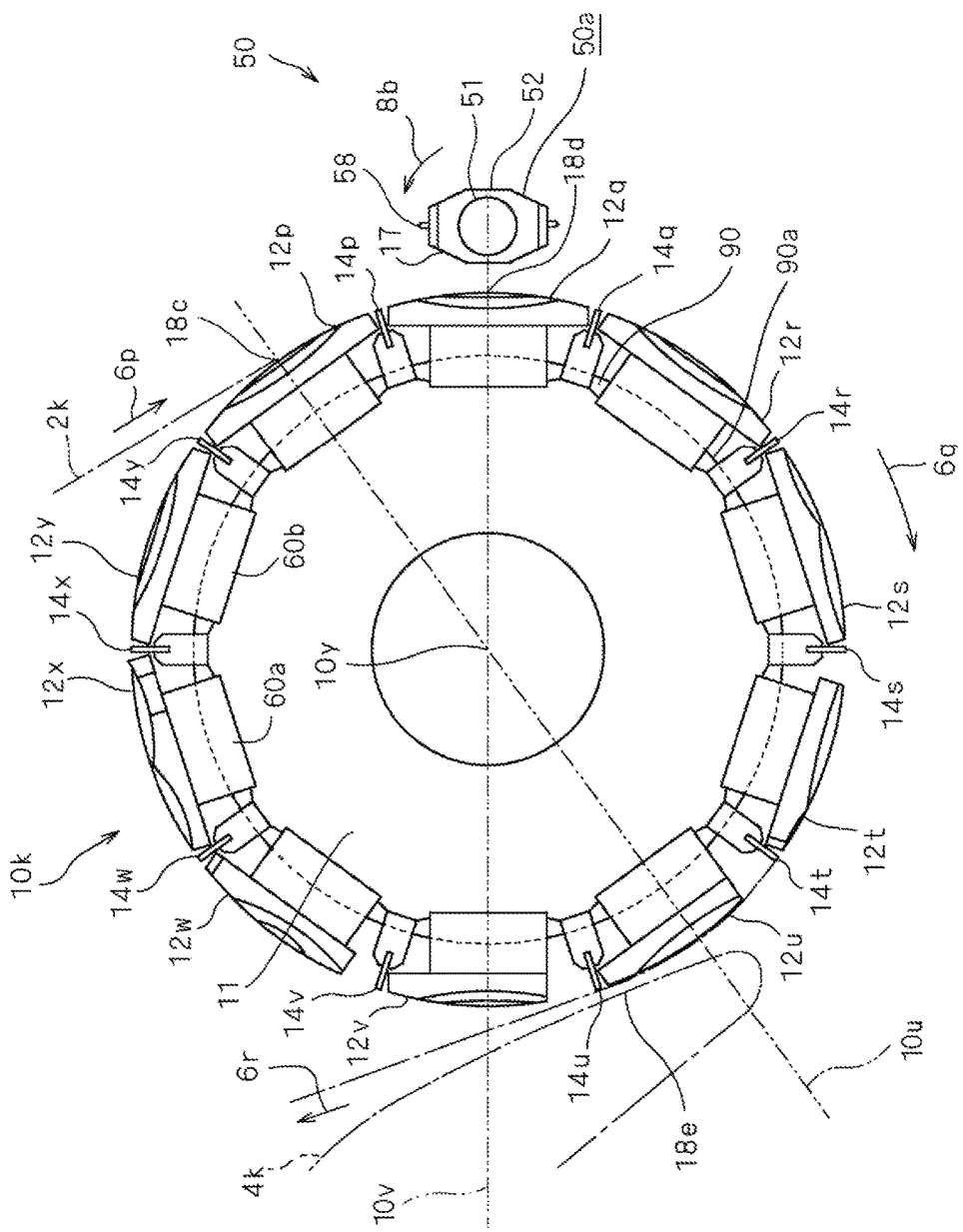
FIG. 1 is a schematic diagram showing the configuration of a conveyance device. (Embodiment 1)

FIG. 1 is a schematic diagram showing the configuration of the conveyance device 10. As shown in FIG. 1, the conveyance device 10 serves also as a web cutting device and then pads 12p to 12y and anvils 14p to 14y are arranged along a cylindrical outer peripheral surface 90a of a stationary drum 90 alternately in the circumferential direction of the outer peripheral surface 90a of the stationary drum 90. Among the pads 12p to 12y, the pads 12p, 12r, 12t, 12v, and 12x in half the number are held by the first travel members 60a and the pads 12q, 12s, 12u, 12w, and 12y in the remaining half are held by the second travel members 60b. A vacuum suction hole (not shown) for vacuum-holding a web 2k serving as a conveyed article is formed in the surface of each of the pads 12p to 12y.

A rotating body 11 serving as a driving member is arranged adjacent to the stationary drum 90. The first and the second travel members 60a and 60b and the anvils 14p to 14y are fixed to the rotating body 11 and then move in the circumferential direction of the outer peripheral surface 90a of the stationary drum 90 as indicated by an arrow 6q in association with revolution of the rotating body 11. Here, a configuration may be employed that the first and the second travel members 60a and 60b are linked to the rotating body 11 through a linkage mechanism and then the first and the second travel members 60a and 60b move along the outer peripheral surface 90a of the stationary drum 90 in the circumferential direction of the stationary drum 90 in association with revolution of the rotating body 11.

At a receiving position 18c, the continuous web 2k is vacuum-held by the pad 12p and then conveyed in the direction indicated by an arrow 6p in association with movement of the pad 12p. Then, in the web 2k, at a cutting position 18d, a portion extending between the pads 12p and 12q adjacent to each other is pinched between the anvil 14q and a blade edge 58a (see FIGS. 2 and 3) of a cutter 58 of a cutting unit 50 revolving in synchronization with conveyance of the web 2k, so as to be cut. That is, the cutter 58 of the cutting unit 50 is held by the revolving member 50a. The revolving member 50a is arranged such that the rotational center axis of the revolving member 50a becomes parallel to the center axis of the stationary drum 90. Then, the revolving member 50a faces, with an interval in between, the web moved in a state of being held by the pads 12p to 12y. The revolving member 50a revolves in the direction indicated by an arrow 8b in synchronization with the movement of the anvils 14p to 14y in such a manner that the cutter 58 faces the anvils 14p to 14y.

An individual piece (a conveyed article; not shown) obtained by cutting from the web is conveyed in a state of being vacuum-held by the pad and then, at a delivery position 18e, the individual piece is transferred from the pad 12u to a device 4k of the subsequent process. The device 4k of the subsequent process conveys the individual piece in the direction indicated by an arrow 6r.

Each of the pads 12p to 12y moves with changing the orientation relative to the circumferential direction of the outer peripheral surface of the stationary drum. That is, in a first interval from the cutting position 18d where the cutter 58 and the anvil face to each other to the delivery position 18e in the moving direction of the pad, the pad changes its orientation by 90° relative to the circumferential direction of the outer peripheral surface of the stationary drum 90. In a second interval from the delivery position 18e to the receiving position 18c in the moving direction of the pad, the pad restores the orientation relative to the circumferential direction of the outer peripheral surface of the stationary drum.

When the first interval is set to be 180° or smaller and the second interval is set to be 180° or smaller, the conveyance device can be constructed in a satisfactory balance. Further, in order that the orientation of the pad may stably be changed, it is preferable that the first and the second interval where the orientation of the pad is changed are made as long as possible and that the distance from the receiving position 18c to the cutting position 18d is made as short as possible. Thus, the delivery position 18e is arranged in an acute angle region between the extension line 10u of the imaginary line joining the center axis 10y of the stationary drum 90 and the receiving position 18c and the extension line 10v of the imaginary line joining the center axis 10y of the stationary drum 90 and the cutting position 18d.

Figure 2:
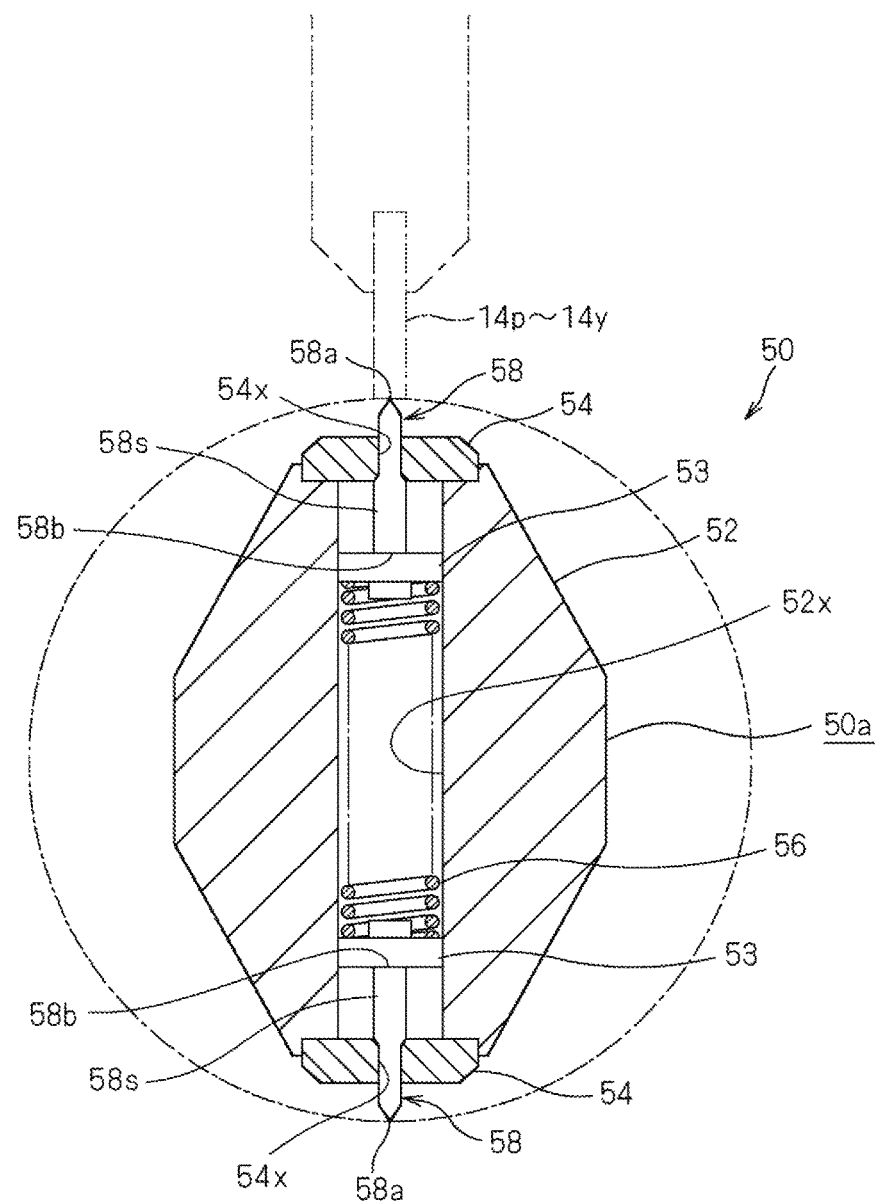
FIG. 2 is a sectional view of a cutting unit. (Embodiment 1)
Figure 3:
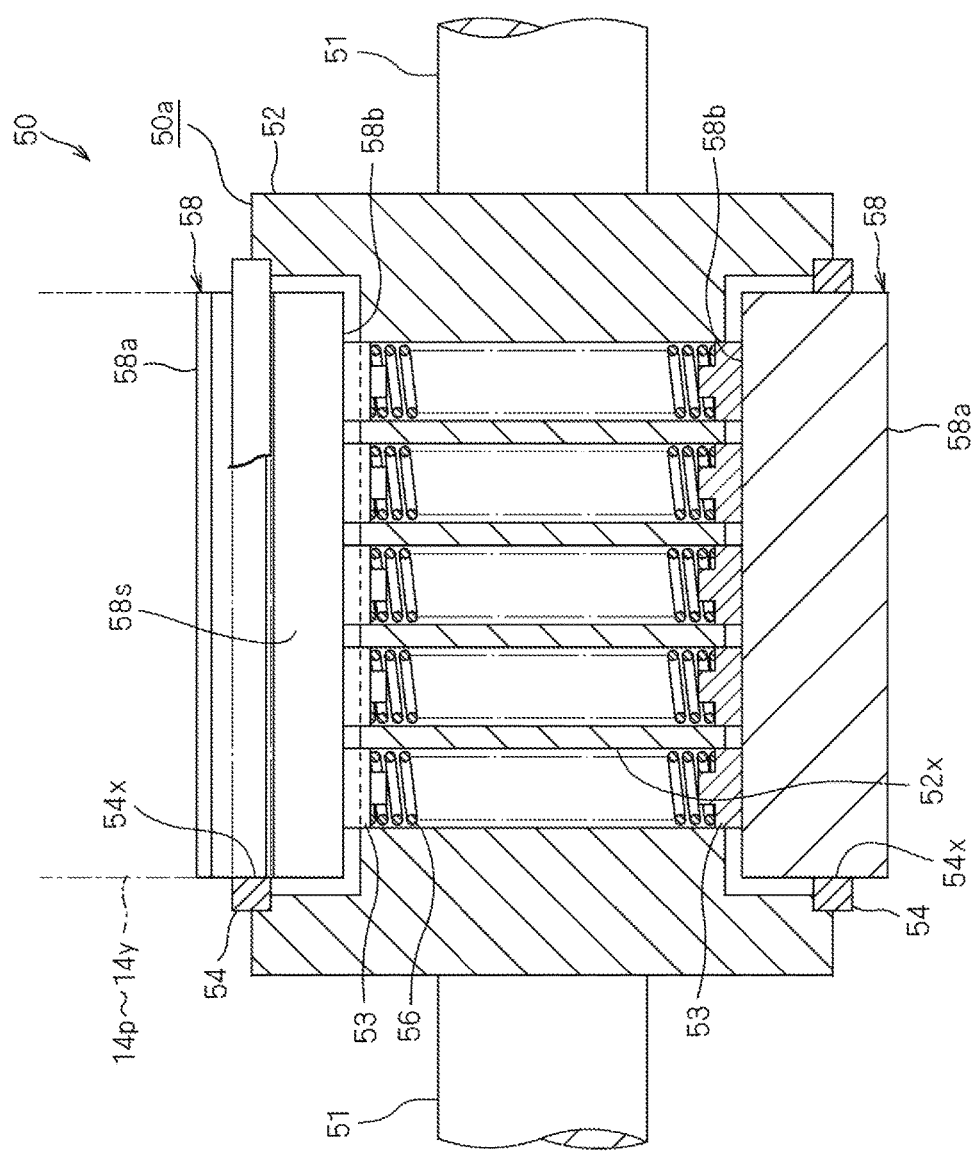
FIG. 3 is a sectional view of a cutting unit. (Embodiment 1)

Next, the cutting unit 50 is described below with reference to FIGS. 2 and 3. FIG. 2 is a sectional view of the cutting unit 50. FIG. 3 is a partly sectional view of the cutting unit 50.

As shown in FIGS. 2 and 3, in the cutting unit 50, a pair of cutters 58 held by a revolving member 50a are biased by helical compression springs 56 arranged in the inside of the revolving member 50a so that the blade edges 58a of the pair of cutters 58 protrude in opposite directions to each other.

The revolving member 50a includes: a body 52 enclosing the center axis of the revolving member 50a; a stop member 54; and a shaft 51 formed integrally with the body 52 and supported in a freely revolvable manner.

In the body 52 of the revolving member 50a, a plurality of through holes 52x are formed that extend perpendicularly to the center axis of the revolving member 50a and pass through the center axis. The helical compression springs 56 are individually arranged in the through holes 52x in a compressed state.

The stop members 54 are respectively fixed to one-end side and the other end side of the through hole 52x of the body 52 of the revolving member 50a. A through hole 54x is formed in the stop member 54.

The cutters 58 are respectively arranged on one-end side and the other end side of the through hole 52x. Then, the blade edge 58a and a portion continuous to the blade edge 58a are inserted into the through hole 54x of the stop member 54, then slide along the inner face of the through hole 54x, and then protrude to the radial-directional outer side of the revolving member 50a. In the cutter 58, the base end 58b side opposite to the blade edge 58a is pinched between the helical compression spring 56 and the stop member 54 with a washer 53 in between so as to be biased to the radial-directional outer side of the revolving member 50a by the helical compression spring 56. The helical compression spring 56 is a biasing member.

In biasing the cutter 58, spring members other than the helical compression springs 56 may be employed. Further, elastic members such as rubber or, alternatively, air cylinders or the like may also be employed. However, spring members are excellent in durability and hence preferable in long-term continuous running. Among such spring members, when the helical compression springs 56 are employed, the configuration of the cutting unit 50 can easily be size-reduced.

The cutter 58 has a bulged part 58s located on the base end 58b side and protruding to the thickness direction both sides in comparison with the blade edge 58a side. The width of the bulged part 58s is greater than the width of the through hole 54x of the stop member 54. Thus, in the cutter 58 biased to the radial-directional outer side of the revolving member 50a by the helical compression springs 56, the bulged part 58s abuts against the stop member 54 so that the protruding position is restricted.

In order that the bulged part 58s of the cutter 58 may abut against the stop member 54, the helical compression springs 56 bias the cutter 58 to the radial-directional outer side of the revolving member 50a to a predetermined position, by a predetermined biasing force corresponding to the compression amount. When a reaction force acting on the cutter 58 is greater than the predetermined biasing force, the helical compression springs 56 are compressed further and thereby allow the cutter 58 to retract from the predetermined position restricted by the stop member 54 to the center side of the revolving member 50a.

When the spring constant and the compression amount of the helical compression springs 56 are appropriately selected, at the time of cutting the web, the interval between the cutter 58 and the anvils 14p to 14y or the abutting of the cutter 58 to the anvils 14p to 14y can easily be adjusted. Further, even when the interval or the abutting between the cutter 58 and the anvils 14p to 14y varies owing to vibration, thermal deformation, or the like during the operation, the interval or the abutting between the cutter 58 and the anvils 14p to 14y is maintained in an appropriately adjusted state. Thus, long-term continuous running can easily be realized.

In the cutting unit 50, the two cutters 58 are attached to the revolving member 50a and then the two cutters 58 alternately cut the web. Thus, the replacement cycle of the cutter can be extended in comparison with a case that one cutter is attached to the revolving member. Further, the common helical compression spring 56 is employed for the two cutters 58 and hence the configuration of the cutting unit 50 becomes simple.

Figure 4:
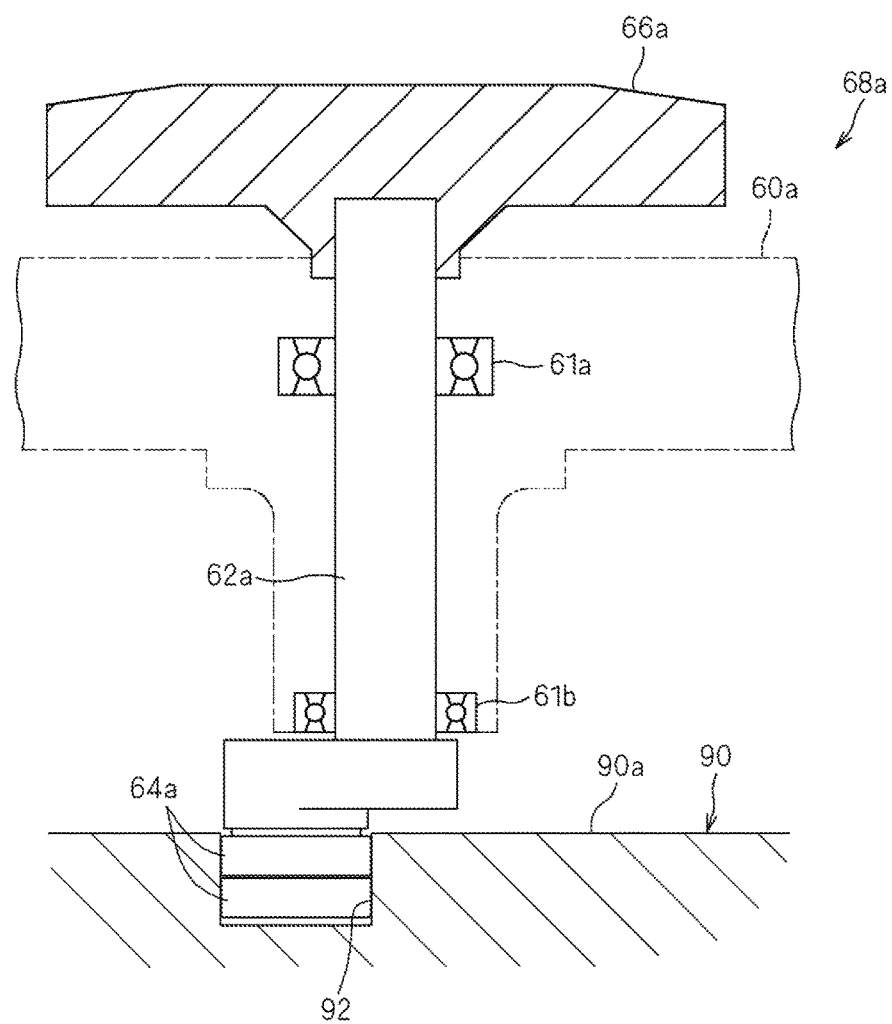
FIG. 4 is a main part sectional view of a first travel member. (Embodiment 1)
Figure 5:
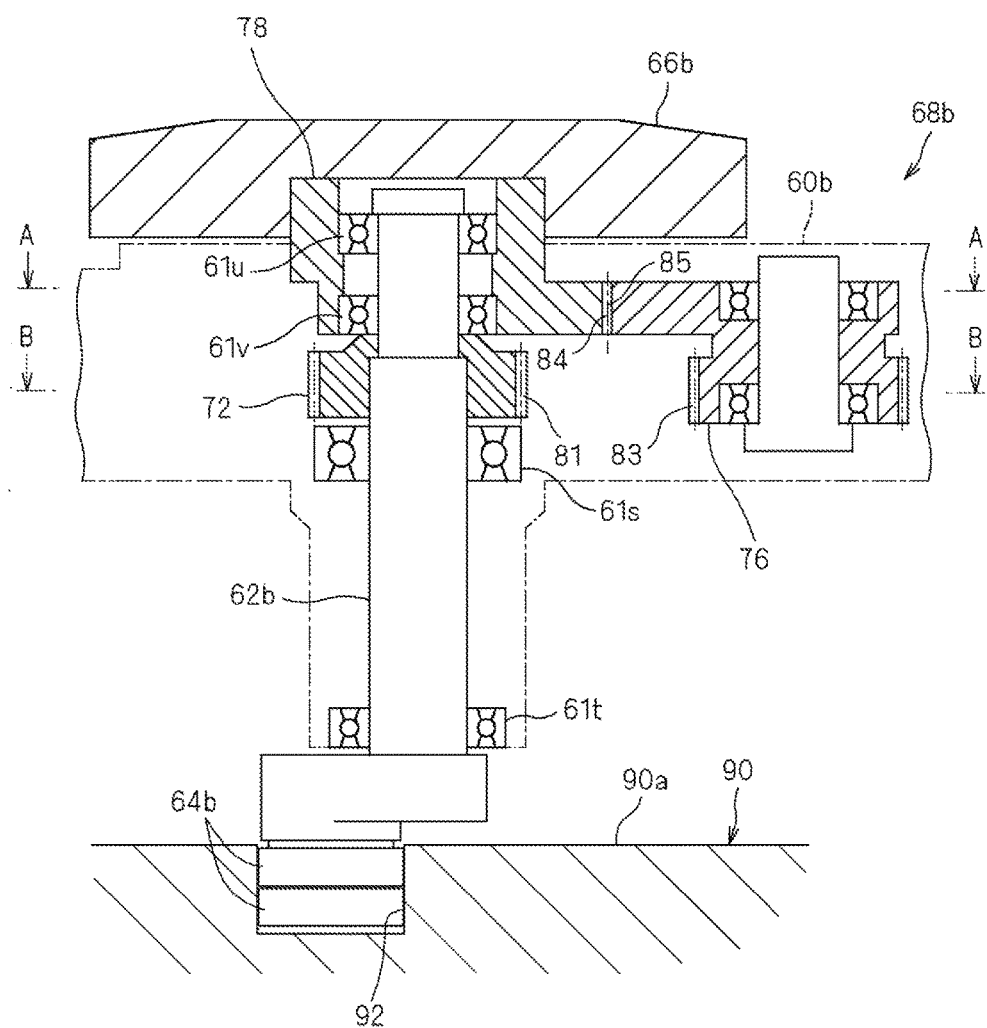
FIG. 5 is a main part sectional view of a second travel member. (Embodiment 1)
Figure 6:
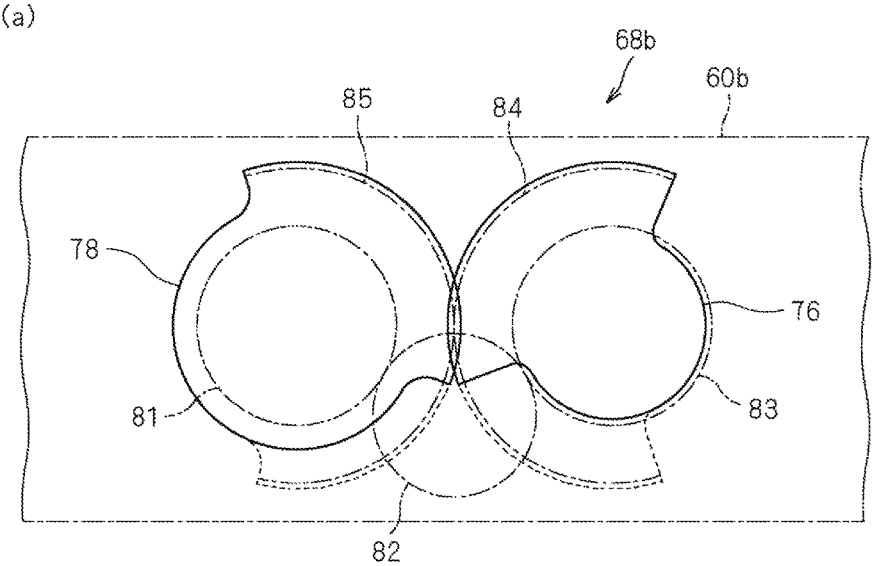
FIGS. 6(a) and 6(b) are main part sectional views of a second travel member. (Embodiment 1)
Figure 6:
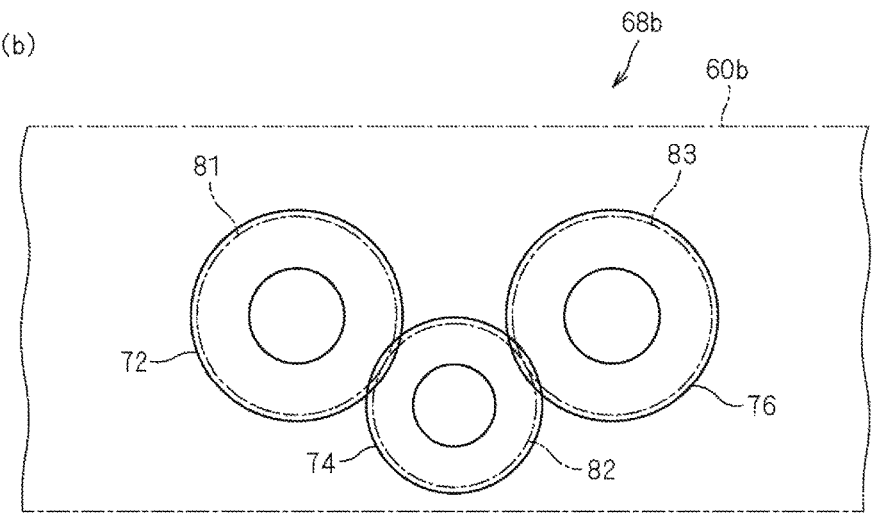

Next, pad rotating mechanisms 68a and 68b for rotating the pads 12p to 12y are described below with reference to FIGS. 4 to 6. FIG. 4 is a main part sectional view of the pad rotating mechanism 68a provided in the first travel member 60a. FIG. 5 is a main part sectional view of the pad rotating mechanism 68b provided in the second travel member 60b. FIG. 6(a) is a main part sectional view taken along line A-A in FIG. 5. FIG. 6(b) is a main part sectional view taken along line B-B in FIG. 5.

The pad 66a shown in FIG. 4 is the first pad held by the first travel member 60a and represents the pads 12p, 12r, 12t, 12v, and 12x in half the number among the pads 12p to 12y shown in FIG. 1. The pad 66b shown in FIG. 5 is the second pad held by the second travel member 60b and represents the pads 12q, 12s, 12u, 12w, and 12y in the remaining half shown in FIG. 1. The number of the first pads and the number of the second pads are the same as each other.

As shown in FIGS. 4 and 5, a cam groove 92 is formed in the outer peripheral surface 90a of the stationary drum 90. The cam groove 92 is a guiding part. As described above, the travel members 60a and 60b individually move in the circumferential direction (a direction perpendicular to the page in FIGS. 4 and 5) of the stationary drum 90 along the outer peripheral surface 90a of the stationary drum 90.

In the travel member 60a or 60b, a shaft member 62a or 62b is supported in a revolvable manner. The shaft member 62a or 62b extends in a radial direction of the stationary drum 90. Then, one end is provided with a cam follower 64a or 64b engaging with the cam groove 92 of the stationary drum 90. The cam follower 64a or 64b is an engagement part. The shaft member 62a or 62b moves together with the travel member 60a or 60b in association with movement of the travel member 60a or 60b. At that time, the cam follower 64a or 64b follows the cam groove 92 so that the shaft member 62a or 62b revolves.

As shown in FIGS. 5 and 6, the pad rotating mechanism 68b for rotating the pad 66b is provided in the second travel member 60b. The pad rotating mechanism 68b includes a shaft member 62b supported in a revolvable manner by the second travel member 60b with bearings 61s and 61t in between. The first gear wheel member 72 is fixed to the middle part of the shaft member 62b and revolves integrally with the shaft member 62b. At the other end of the shaft member 62b on the opposite side to the one end provided with the cam follower, a fourth gear wheel member 78 is supported coaxially to the shaft member 62b in a revolvable manner with bearings 61u and 61v in between. Further, a second and a third gear wheel member 74 and 76 are arranged in parallel to the shaft member 62b and then supported in a revolvable manner by the second travel member 60b.

A first gear wheel 81 is formed in the first gear wheel member 72. A second gear wheel 82 engaging with the first gear wheel is formed in the second gear wheel member 74. In the third gear wheel member 76, a third gear wheel 83 engaging with the second gear wheel 82 and a fourth gear wheel 84 are formed coaxially to each other. A fifth gear wheel 85 engaging with the fourth gear wheel 84 is formed in the fourth gear wheel member 78. When the shaft member 62b revolves, the third gear wheel member 76 revolves in the same direction as the shaft member 62b by virtue of the engagement of the first to the third gear wheel 81 to 83. The fourth gear wheel member 78 revolves in the opposite direction to the third gear wheel member 76 by virtue of the engagement of the fourth and the fifth gearwheel 84 and 85. That is, the fourth gear wheel member 78 revolves in the opposite direction to the shaft member 62b.

For example, the first gear wheel 81 and the third gear wheel 83 are constructed such as to have the same number of gear teeth as each other. Then, the reduction gear ratio achieved by the fourth gear wheel 84 and fifth gear wheel 85 are set to be 1. In this case, in accordance with the movement of the travel member 60b, the shaft member 62b reciprocally rotates within a range of 90° so that the third and the fourth gear wheel member 76 and 78 rotate within a range of 90° between a position indicated by a solid line in FIG. 6 and a position indicated by a dashed line.

As shown in FIG. 5, the pad 66b is fixed to the fourth gear wheel member 78. The pad 66b rotates integrally with the fourth gear wheel member 78 in the opposite direction to the shaft member 62b. The pad rotating mechanism 68b for rotating the pad 66b is an opposite-directional pad rotating mechanism. The pad 66b is supported in a revolvable manner by the second travel member 60b with the shaft member 62b, the bearings 61u and 61v, and the fourth gear wheel member 78 in between.

On the other hand, as shown in FIG. 4, the pad rotating mechanism 68a for rotating the pad 66a is provided in the first travel member 60a. The pad rotating mechanism 68a includes a shaft member 62a supported in a revolvable manner by the first travel member 60a with bearings 61a and 61b in between. The pad 66a is fixed to the other end of the shaft member 62a. The pad 66a rotates integrally with the shaft member 62a and rotates in the same direction as the shaft member 62a. The pad rotating mechanism 68a for rotating the pad 66a is an identical-directional pad rotating mechanism.

That is, among the pads 66a and 66b, the first pad 66a that revolves when revolution of the shaft member 62a supported in a revolvable manner by the first travel member 60a is transmitted and the second pad 66b that revolves when revolution of the shaft member 62b supported in a revolvable manner by the second travel member 60b is transmitted rotate in opposite directions to each other during the time from the start of holding of the web serving as a conveyed article to the release of the individual piece of the web.

Further, as shown in FIG. 1, the total number of pads is even. Then, among the pads, the first pads 66a (see FIG. 4) in half the number and the second pads 66b (see FIG. 5) in the remaining half are arranged alternately in the circumferential direction of the stationary drum 90.

Thus, after cutting the web, the conveyance device 10 can transfer the individual pieces obtained by cutting from the web, to the subsequent device in a state that the orientations are alternately changed. The cam groove 92 serving as a guiding part is common to each other. Further, it is sufficient that the pad rotating mechanism 68b having a complicated configuration including the first to the fifth gear wheel 81 to 85 is provided in each of the second travel members 60b, that is, in half the number of the travel members 60a and 60b. Thus, the configuration of the conveyance device 10 becomes simple.

The first pad 66a is directly connected to the shaft member 62a supported in a revolvable manner by the first travel member 60a. Thus, any mechanism for transmitting the revolution is not provided between the shaft member 62a and the first pad 66a. Thus, the configuration of transmitting the revolution of the shaft member 62a so as to rotate the pad 66a can be simplified.

The second pad 66b rotates coaxially to the shaft member 62b supported in a revolvable manner by the second travel member 60b. Thus, a configuration can easily be constructed that the first pad 66a and the second pad 66b rotate in opposite directions to each other. The first to the fifth gear wheel 81 to 85 of the pad rotating mechanism 68b are excellent in durability in comparison with a belt, a chain, or the like and hence are preferable in long-term continuous running.

Next, a conveyance method of conveying the web 2k by using the conveyance device 10 is described below.

The conveyance method includes a first to a fourth step.

At the first step, the first and the second pads 66a and 66b in the same number as each other arranged along the cylindrical outer peripheral surface 90a of the stationary drum 90 where the cam groove 92 is formed as a guiding part and arranged alternately in the circumferential direction of the outer peripheral surface 90a are moved in the circumferential direction of the outer peripheral surface 90a. Further, the anvils individually arranged between the first and the second pads 66a and 66b adjacent to each other are moved together with the first and the second pads 66a and 66b.

At the second step, the first and the second pads 66a and 66b moving at the first step start holding of the continuous web 2k at the receiving position 18c and then release the holding of the web in the form of individual pieces at the delivery position 18e so as to convey the web from the receiving position 18c to the delivery position 18e.

At the third step, in each pad of both the first and the second pads 66a and 66b moving with holding the web at the second step, rotation generated by engagement between the cam follower 64a or 64b that moves together with each pad and the cam groove 92 is transmitted to each pad so that each pad rotates and follows the cam groove 92. Then, by virtue of a difference in the rotation of the first and the second pads 66a and 66b, the orientations of the webs which were the same in the first and the second pads 66a and 66b at the receiving position 18c where holding of the web is started are made different in the first pads 66a and in the second pads 66b at the delivery position 18e where holding of the web is released. The rotations of the first and the second pads 66a and 66b that follow the cam groove 92 start after passing through the cutting position of 18d between the receiving position 18c and the delivery position 18e. Then, the first and the second pads 66a and 66b rotate in opposite directions to each other with following the cam groove 92.

At the fourth step, in a state that the cutter 58 is held by the revolving member 50a and then the cutter 58 is biased to a predetermined position by a biasing force from the helical compression spring 56 serving as a biasing member arranged in the revolving member 50a so that the blade edge 58a of the cutter 58 is caused to protrude, the revolving member 50a is revolved in synchronization with the conveyance of the web at the second step and then at the cutting position 18d, a to-be-cut portion of the web that extends between the first and the second pad 66a and 66b adjacent to each other is pinched between the blade edge 58a of the cutter 58 and the anvil 14p to 14y so as to be cut.

In the method described above, the first and the second pads 66a and 66b are in the same number as each other. Thus, the total number of the pads 66a and 66b is even. Since the first and the second pads 66a and 66b rotate with following the cam groove 92, transfer can be performed with alternately changing the orientations of the conveyed articles by employing a simple configuration.

Further, the angle difference between the first and the second pad 66a and 66b at the time that the first and the second pads 66a and 66b rotate in opposite directions to each other with following the cam groove 92 can be made twice of a case that either alone of the first and the second pads 66a and 66b rotate with following the cam groove 92. The first and the second pads 66a and 66b can be rotated by the common cam groove 92. It is sufficient that a mechanism for converting the rotation into the opposite direction is provided in either of the first and the second pads 66a and 66b, that is, in half the number of the pads. Thus, the orientations of the conveyed articles at the time of transfer of the conveyed articles can alternately be changed by employing a simple configuration.

Further, by virtue of the fourth step, after the continuous web 2k is cut into the form of individual pieces, the individual pieces can be transferred with alternately changing the orientations. Even when the interval between the blade edge 58a of the cutter 58 and the anvil 14p to 14y or the abutting of the blade edge 58a of the cutter 58 varies owing to vibration, thermal deformation, or the like during the operation, at the time of cutting the web 2k, the abutting can be maintained within an appropriate adjustment range. Thus, long-term continuous running becomes easy.

Specifically, at the first step, the first and the second travel members 60a and 60b in the same number as each other that holds the first and the second pads 66a and 66b and that are arranged along the outer peripheral surface 90a of the stationary drum 90 alternately in the circumferential direction of the outer peripheral surface 90a are moved in the circumferential direction of the outer peripheral surface 90a. At the third step, the pad rotating mechanisms 68a and 68b are provided in the individual travel members of the first and the second travel members 60a and 60b. The pad rotating mechanism 68a or 68b includes the shaft member 62a or 62b that is provided with the cam follower 64a or 64b engaging with the cam groove 92, is supported by each travel member in a revolvable manner, and moves together with each travel member. Then, by virtue of the revolution of the shaft member 62a or 62b associated with the movement of each travel member, the pad 66a or 66b held by each travel member is rotated about the shaft center extending in the radial direction of the outer peripheral surface 90a of the stationary drum 90.

By virtue of this, by employing a simple configuration, the first and the second pads 66a and 66b can be moved in the circumferential direction of the outer peripheral surface 90a of the stationary drum 90 or, alternatively, rotated about the shaft center extending in the radial direction of the outer peripheral surface 90a of the stationary drum 90.

Here, in place of the cam groove 92 as a guiding part, employable are: a cam having a linear rim shape protruding from the outer peripheral surface 90a of the stationary drum 90; gear teeth having a rack shape; or the like. The outer peripheral surface in which the guiding part such as the cam groove 92 is formed may be a virtual surface. The engagement part may be any mechanism rotating with engaging with the guiding part, and hence is not limited to the cam follower. Thus, a gear wheel or the like may be employed. The pad rotating mechanism is not limited to a gear wheel train and may include a pulley, a timing belt, a linkage mechanism, or the like. In the pad rotating mechanism, the engagement part and the pad may be linked together in a decentered manner in place of a coaxial manner. The conveyed article may be held by the pad by a method other than the vacuum holding, like a pushing member is employed for pressing against the pad the conveyed article in contact with the pad.

Embodiment 2

A conveyance device and a conveyance method of Embodiment 2 are described below with reference to FIG. 7. The conveyance device of Embodiment 2 has a substantially similar configuration to the conveyance device of Embodiment 1. The following description is given with focusing on the difference from Embodiment 1. Thus, like components to Embodiment 1 are designated by like numerals.

Figure 7:
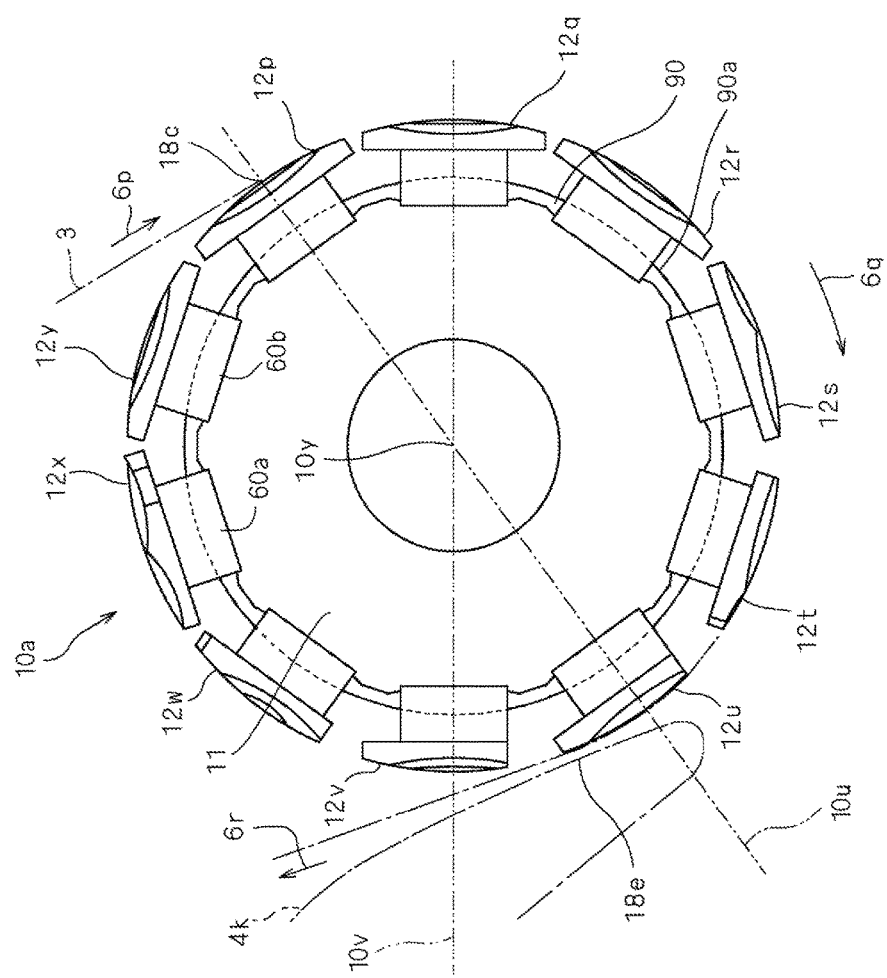
FIG. 7 is a schematic diagram showing the configuration of a conveyance device. (Embodiment 2)

FIG. 7 is a schematic diagram of a conveyance device 10a of Embodiment 2. As shown in FIG. 7, the conveyance device 10a of Embodiment 2 does not include the anvils 14p to 14y and the cutting unit 50 of the conveyance device 10 of Embodiment 1 (see FIG. 1).

In the conveyance device 10a, conveyed articles in the form of individual pieces conveyed along a conveyance path 3 in the direction indicated by an arrow 6p are successively received by the pads 12p to 12y and then during the conveyance of the conveyed articles, the pads 12p to 12y rotate them alternately in opposite directions to each other. By virtue of this, the conveyed articles are transferred to the device 4k of the subsequent process in a state that the orientations of the conveyed articles are alternately changed.

In a conveyance method of Embodiment 2, at the third step, holding of conveyed articles which are in the form of individual pieces from the beginning is started. Thus, the conveyance method of Embodiment 2 does not include the fourth step of cutting the continuous web 2k during the conveyance. Further, the anvils are unnecessary. Further, at the third step, the first and the second pads may start rotation with following the cam groove 92 at an arbitrary timing in the course of moving from the receiving position to the delivery position.

Embodiment 3

A conveyance device and a conveyance method of Embodiment 3 are described below with reference to FIGS. 8 and 9. The conveyance device of Embodiment 3 has a substantially similar configuration to the conveyance device 10a of Embodiment 2. The following description is given with focusing on the difference from the conveyance devices 10 and 10a and the conveyance methods of Embodiments 1 and 2.

Figure 8:
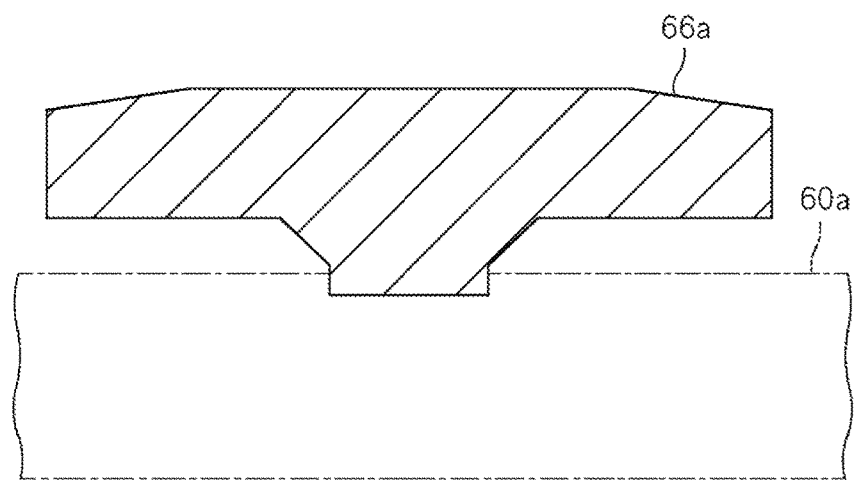
FIG. 8 is a main part sectional view of a first travel member. (Embodiment 3)
Figure 8:
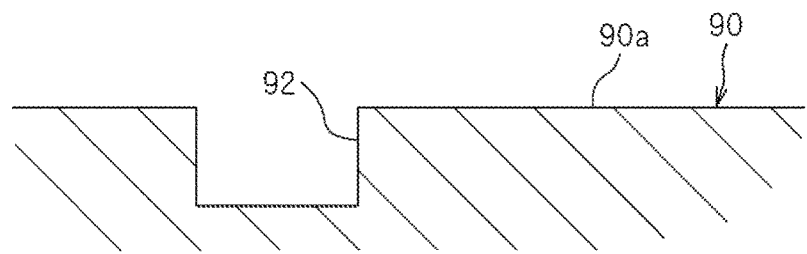

FIG. 8 is a main part sectional view of a first travel member 60a of the conveyance device of Embodiment 3. As shown in FIG. 8, a pad 66a is fixed to the first travel member 60a. The pad 66a does not rotate even when the first travel member 60a moves. That is, a pad rotating mechanism is not provided in the first travel member 60a.

Figure 9:
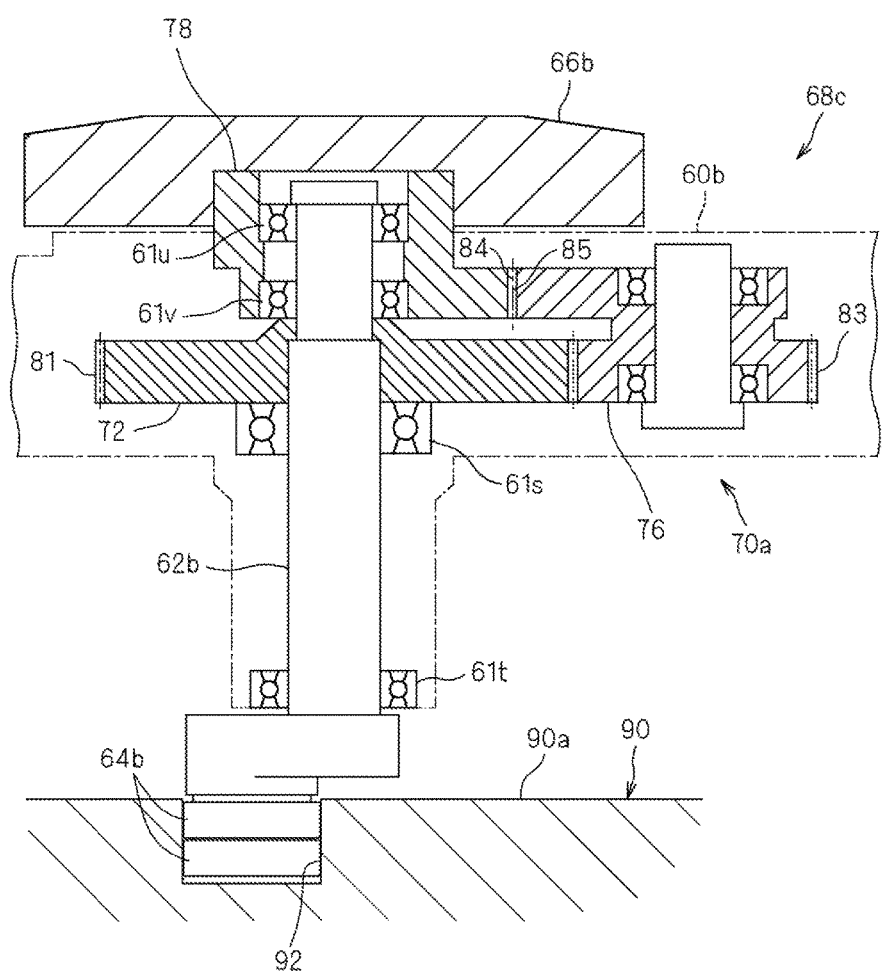
FIG. 9 is a main part sectional view of a second travel member. (Embodiment 3)
Figure 10:
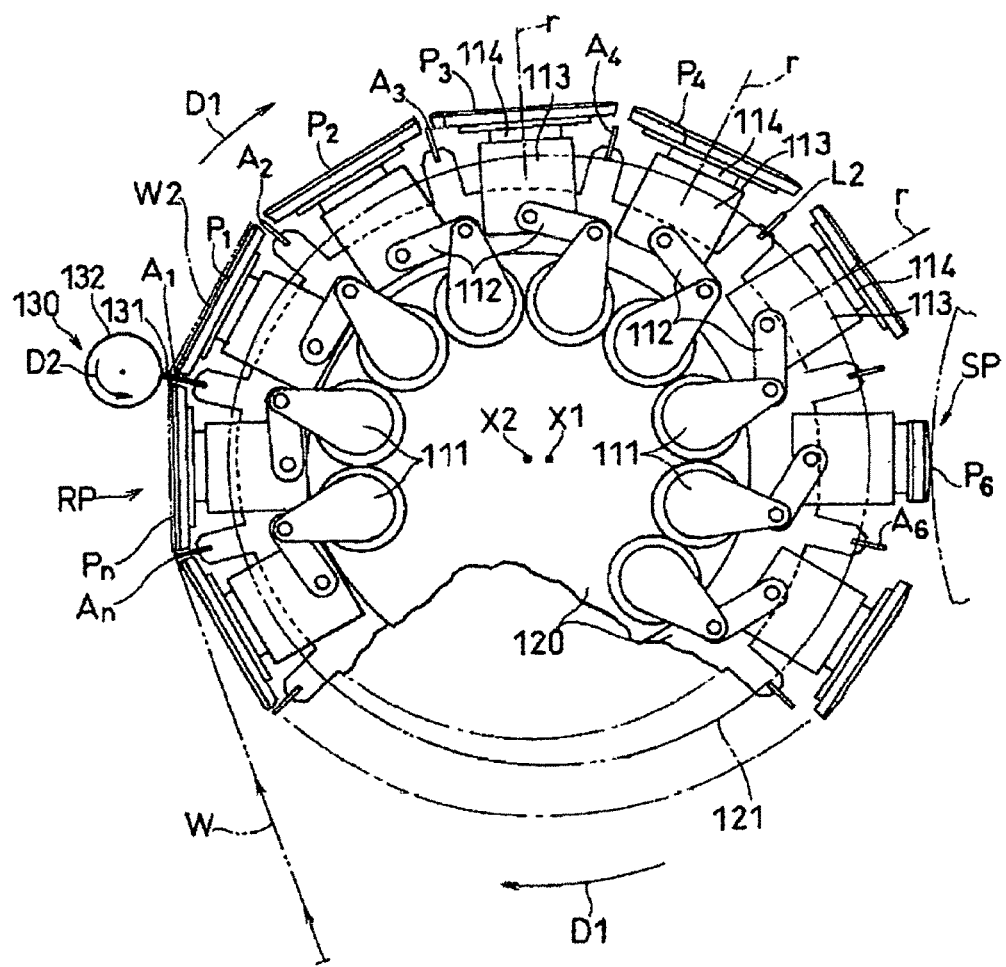
FIG. 10 is a schematic diagram showing the configuration of a conveyance device. (Conventional Example 1)
Figure 11:
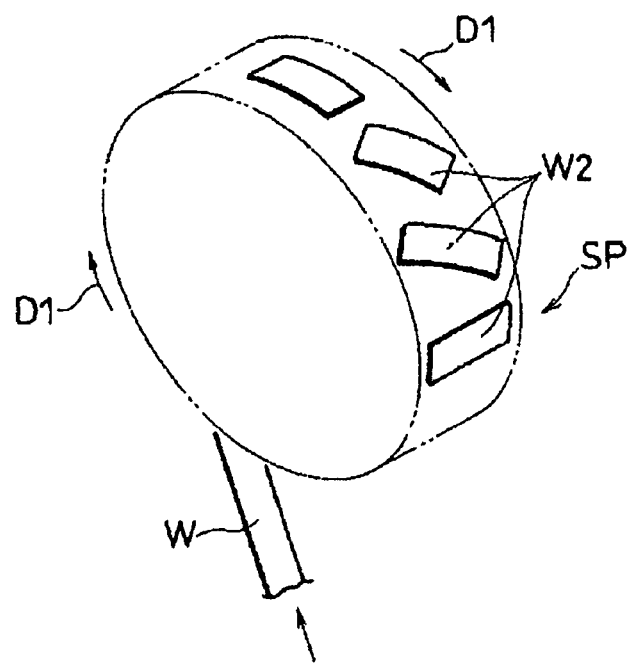
FIG. 11 is a schematic perspective view showing the state of carrying a web. (Conventional Example 1)

FIG. 9 is a main part sectional view of a second travel member 60b of the conveyance device of Embodiment 3. As shown in FIG. 9, the second travel member 60b is provided with a pad rotating mechanism 68c having a substantially similar configuration to the pad rotating mechanism 68b of Embodiment 1 shown in FIG. 6. That is, similarly to the pad rotating mechanism 68b of Embodiment 1, the pad rotating mechanism 68c includes a shaft member 62b supported by the second travel member 60b in a freely revolvable manner. The shaft member 62b includes a cam follower 64b engaging with the cam groove 92 of the stationary drum 90. The shaft member 62b rotates in association with the movement of the second travel member 60b. The second travel member 60b supports the second pad 66b coaxially to the shaft member 62b in a freely revolvable manner. The second pad 66b rotates when the revolution of the shaft member 62b is transmitted through the pad rotating mechanism 68c.

The pad rotating mechanism 68c has a similar configuration to the pad rotating mechanism 68b of Embodiment 1 except for a point that the second gear wheel 82 of the pad rotating mechanism 68b of Embodiment 1 shown in FIG. 6 is not provided and hence the first gear wheel 81 and the third gear wheel 83 directly engage with each other. The numbers of gear teeth in the gear wheels 81, 83, 84, and 85 of the pad rotating mechanism 68c are appropriately selected so that, for example, the reciprocal rotation within a range of 90° of the shaft member 62b is extended into twice by the pad rotating mechanism 68c. Thus, a configuration is realized that the pad 66b reciprocally rotates within a range of 180°.

Similarly to Embodiment 1, in the conveyance device of Embodiment 3, the first and the second travel members 60a and 60b are arranged alternately to each other. After receiving the conveyed article, the pad 66a fixed to the first travel member 60a transfers the conveyed article without changing the orientation. On the other hand, after receiving the conveyed article, the pad 66b fixed to the second travel member 60b transfers the conveyed article with inverting the orientation by 180°. In the conveyance device of Embodiment 3, the first and the second travel members 60a and 60b are arranged alternately and the pads 66a and 66b are arranged alternately. Thus, transfer can be performed with alternately changing the orientations of the conveyed articles.

In contrast to the conveyance method of Embodiments 1 and 2, in the conveyance method of Embodiment 3, at the third step, one kind of pads 66b alone among the first and the second pads 66a and 66b are rotated with following the cam groove 92 by employing the pad rotating mechanism.

Also in this case, transfer can be performed with alternately changing the orientations of the conveyed articles by employing a simple configuration.

CONCLUSION

As described above, in the conveyance device and the conveyance method of Embodiments 1 to 3, transfer can be performed with alternately changing the orientations of the conveyed articles by employing a simple configuration.

Here, the present invention is not limited to the modes of implementation given above and may be implemented with various changes.

For example, a member like the pad described in the form of a single member in the embodiments may be constructed from a single component part or, alternatively, from a plurality of component parts integrated into a single member.

In Embodiment 1, the first pad has been fixed to the other end of the shaft member supported by the first travel member in a revolvable manner. Instead, the first travel member may be provided with a rotation transmitting mechanism for transmitting to the first pad the revolution of the same direction as the shaft member.

A configuration without the stationary drum may be employed. For example, a configuration may be employed that pads and anvils are held along a revolving drum and then the revolving drum revolves so that the pads and the anvils are moved along a cylindrical movement path in the circumferential direction. Further, the cylindrical outer peripheral surface in which the guiding part is formed may be a virtual surface.

DESCRIPTION OF REFERENCE NUMERALS 10, 10a Conveyance device
11 Rotating body (driving member)
12p to 12y Pad
14p to 14y Anvil
52 Revolving member
56 Helical compression spring (biasing member)
58 Cutter
58a Blade edge
60a, 60b Travel member
62a, 62b Shaft member
64a 64b Cam follower (engagement part)
66a First pad
66b Second pad
68a Pad rotating mechanism (identical-directional pad rotating mechanism)
68b Pad rotating mechanism (opposite-directional pad rotating mechanism)
68c Pad rotating mechanism
81 First gear wheel
82 Second gear wheel
83 Third gear wheel
84 Fourth gear wheel
85 Fifth gear wheel
90 Stationary drum
90a Outer peripheral surface
92 Cam groove (guiding part)

The invention claimed is:
1. A conveyance device comprising:
a guiding part formed in a cylindrical outer peripheral surface;
a plurality of first travel members arranged along the outer peripheral surface and moving in a circumferential direction of the outer peripheral surface;
a plurality of second travel members having a number same as a number of the first travel members, each of the second travel members being arranged between the first travel members adjacent to each other and moving in the circumferential direction together with the first travel members;
a plurality of pads individually held by the first and the second travel members and moving together with the first and the second travel members, each pad of the plurality of pads being configured to receive and hold a conveyed article at a receiving position and to release the conveyed article at a delivery position; and
a plurality of pad rotating mechanisms provided in the plurality of first and second travel members, respectively,
each pad rotating mechanism including a shaft member supported rotatably by the travel member, and moving together with the travel member, the shaft member including an engagement part engaging with the guiding part and rotating in association with a movement of the travel member, so that rotational directions of the shaft members are identical to each other when moving from the receiving position to the delivery position, said each pad rotating mechanism rotating the pad held by the travel member about a shaft center extending in a radial direction of the outer peripheral surface in association with a rotation of the shaft member so that the pads held by the first travel members and the pads held by the second travel members rotate differently from each other from the receiving position to the delivery position,
the plurality of pad rotating mechanisms further including identical-directional pad rotating mechanisms, each being provided in each of the first travel members and transmitting the rotation of the shaft member to the pad held by each of the first travel members so that a rotational direction of the pad held by the first travel member is identical to that of the shaft member, and
opposite-directional pad rotating mechanisms, each being provided in each of the second travel members and transmitting the rotation of the shaft member to the pad held by each of the second travel members so that a rotational direction of the pad held by the second travel member is opposite to that of the shaft member,
wherein the pads held by the first travel members and the pads held by the second travel members are configured so that
orientations of the conveyed articles held by the pads of the first travel members are same as orientations of the conveyed articles held by the pads of the second travel members at the receiving position, and
the orientations of the conveyed articles held by the pads of the first travel members are different from the orientations of the conveyed articles held by the pads of the second travel members at the delivery position, the pad held by each of the first travel members and the pad held by each of the second travel members rotate in opposite directions to each other, the pad held by each of the first travel members is fixed coaxially to the shaft member of the identical-directional pad rotating mechanism, and the pad held by each of the second travel members is held by the second travel member and in a coaxial and relatively rotatable manner relative to the shaft member of the opposite-directional pad rotating mechanism.

2. The conveyance device according to claim 1, wherein the conveyed article is a continuous web, the conveyance device further comprises:
- a plurality of anvils arranged between the first and the second travel members adjacent to each other and moving together with the first and the second travel members in the circumferential direction;
- a revolving member that is arranged, with an interval in between, opposite to the web moved in a state of being held by the pads and that revolves in synchronization with movement of the anvils; and
- a cutter which is held by the revolving member and includes a blade edge protruding to an outer side of the revolving member in which the blade edge faces the anvil in association with revolution of the revolving member, and the blade edge of the cutter and the anvil pinch to cut a portion of the web held by the pads and extending between the pads adjacent to each other.

3. The conveyance device according to claim 1, wherein each of the plurality of pad rotating mechanisms transmits the rotation of the shaft member to the pad through a gear wheel.

4. The conveyance device according to claim 1, wherein the opposite-directional pad rotating mechanism includes:
- a first gear wheel rotating integrally with the shaft member held by each of the second travel members;
- a fifth gear wheel rotating integrally with the second pad held by each of the second travel members;
- a second gear wheel supported by each of the second travel members in a revolvable manner and engaging with the first gear wheel;
- a fourth gear wheel supported by each of the second travel members in a rotational manner and engaging with the fifth gear wheel; and
- a third gear wheel engaging with any one of the second gear wheel and the fourth gear wheel and rotating coaxially to and integrally with the other one of the second gear wheel and the fourth gear wheel.

* * * * *